US009089721B1

(12) United States Patent
Horstman et al.

(10) Patent No.: US 9,089,721 B1
(45) Date of Patent: Jul. 28, 2015

(54) OXYGEN GENERATING SYSTEM

(75) Inventors: Raymond H. Horstman, Snohomish, WA (US); Chao-Hsin Lin, Redmond, WA (US)

(73) Assignee: The Boeing Company, Chicago, IL (US)

( * ) Notice: Subject to any disclaimer, the term of this patent is extended or adjusted under 35 U.S.C. 154(b) by 673 days.

(21) Appl. No.: 13/426,763

(22) Filed: Mar. 22, 2012

(51) Int. Cl.
*A61M 11/00* (2006.01)
*A62B 7/14* (2006.01)

(52) U.S. Cl.
CPC .................................. *A62B 7/14* (2013.01)

(58) Field of Classification Search
CPC .......... A62B 7/14; A62B 25/005; A62B 7/02; A62B 9/02; A62B 21/00; A64D 11/00; A64D 2231/02; A64D 13/00
See application file for complete search history.

(56) References Cited

U.S. PATENT DOCUMENTS 3,179,119 A * 4/1965 Fitt et al. .................... 137/81.1
4,499,914 A * 2/1985 Schebler .................... 137/81.1
4,651,728 A * 3/1987 Gupta et al. ............ 128/201.28
4,919,124 A * 4/1990 Stevenson et al. ....... 128/202.26
5,004,485 A 4/1991 Hamlin et al.
5,199,423 A 4/1993 Harral et al.
5,247,926 A 9/1993 Harral
5,269,295 A 12/1993 Foote et al.
5,351,682 A 10/1994 Foote
5,460,175 A 10/1995 Foote et al.
5,701,889 A 12/1997 Danon
5,881,725 A 3/1999 Hoffman et al.
6,701,923 B2 3/2004 Cazenave et al.
6,792,846 B2 9/2004 Barrett
6,883,247 B2 4/2005 Barrett
6,948,498 B2 9/2005 Cazenave et al.
6,955,710 B2 10/2005 Lessi et al.
7,255,104 B2 8/2007 Phillips
7,264,647 B2 9/2007 Meckes et al.
7,341,072 B2 3/2008 Talty
7,617,826 B1 11/2009 Voege et al.
7,981,193 B2 * 7/2011 Hedges ............................ 95/8
8,517,018 B2 * 8/2013 Wenzel et al. .......... 128/205.14

* cited by examiner

*Primary Examiner* — Steven Douglas
(74) *Attorney, Agent, or Firm* — Parsons Behle & Latimer

(57) ABSTRACT

A system for providing oxygen includes an oxygen generating device, configured to provide oxygenated air, a monitor of a condition of the air provided by the oxygen generating device, a backup oxygen supply, and an automatic switch. The automatic switch is configured to activate the backup oxygen supply and block air from the oxygen generating device when the monitor detects a failure of the condition of the air provided by the oxygen generating device. The system can be used for providing backup oxygen in an aircraft.

16 Claims, 10 Drawing Sheets

OXYGEN GENERATING SYSTEM

FIELD

The present disclosure relates to oxygen generating systems. More particularly, the present disclosure relates to a backup oxygen generating system that monitors contaminant levels in an oxygen generating system, and can include a pristine independent oxygen backup, and emergency air supply for purging.

BACKGROUND

The statements in this section merely provide background information related to the present disclosure and may not constitute prior art.

Modern aircraft operate at altitudes at which there is insufficient oxygen to sustain normal human conscious activities. At high altitudes, pressurized aircraft cabins or cockpits are typically provided with a cabin pressurizing and ventilating system that maintains an environment equivalent to standard atmospheric pressure at an elevation of approximately 8,000 feet. The environmental equivalent altitude is referred to as "cabin altitude." Since the relative proportion of oxygen in earth's atmosphere is relatively constant, regardless of altitude, a satisfactory aircraft cabin environment is maintained simply by taking in atmospheric air from outside the aircraft and compressing it. In cabin pressurizing and ventilating systems, fresh pressurized air is supplied to the cabin or cockpit from an air pressure source, such as using engine bleed air, or by using a separate air pump, supercharger, auxiliary power unit (APU) or the like, to draw in atmospheric air. Air pressure within the cabin is maintained at the required pressure by controlling the flow of air out of the cabin through one or more outflow valves in the aircraft.

For emergency conditions, however, a supply of oxygen is needed. In military aircraft, such as fighter aircraft, the pilot or pilots are permanently supplied by an on-board oxygen generating system (commonly abbreviated to OBOGS), using a zeolite-type molecular sieve to separate gases from the air. In commercial aircraft, zeolite-type oxygen generation systems can also be used to provide emergency oxygen for the passengers and crew. If cabin pressure is lost, or the cabin environment or air supply is contaminated in some way (e.g. by smoke or other toxins), oxygen masks can be deployed for use by the aircraft crew and passengers until such time as the aircraft descends to a safe altitude (e.g. below 10,000 feet) and/or the cabin contamination problem is resolved through venting, etc. While failures of emergency oxygen systems are relatively rare, they are still possible. In the event of such a failure, persons using the system can be quickly overcome by hypoxia and other dangerous conditions. Engine bleed system or APU contamination or failure also present possible avenues for contamination of emergency air or loss of sufficient oxygen.

Unfortunately, many aircraft are not provided with a backup oxygen supply in case of such failure. For example, many systems do not have an independent, pristine backup oxygen supply. On the other hand, in some systems the backup oxygen may be charged by the primary on-board oxygen-generating system, and thus can contain the same contaminants. Additionally, while some systems provide oxygen and pressure sensors, these systems often depend on crew action, and do not automatically engage. In military aircraft, the pilot and crew will normally have an oxygen mask donned at high altitude, but may not notice a signal from an oxygen performance monitor, particularly during a combat situation when their attention is directed elsewhere. In such cases, where an oxygen mask is normally worn, contamination of the oxygen supply can very rapidly affect pilot performance and safety. Additionally, in some cases crew action may be limited to a quick descent that could cause back pressure on the system at low engine settings, which can hinder its performance.

The present disclosure is directed toward one or more of the above-mentioned issues.

SUMMARY

In one embodiment, the present disclosure provides a system for providing oxygen, which includes an oxygen generating device, configured to provide oxygenated air, a monitor of a condition of the air provided by the oxygen generating device, a backup oxygen supply, and an automatic switch. The automatic switch is configured to activate the backup oxygen supply when the monitor detects a failure of the condition of the air provided by the oxygen generating device.

In one specific embodiment, the monitor is configured to detect at least one of a carbon monoxide (CO) level, an oxygen ($O_2$) level, hydrocarbons, and a flow rate in an outlet of the oxygen generating device.

In another specific embodiment, the system includes a ram inlet, a monitor of ram pressure, and a ventilation system controller. The ventilation system controller opens the ram inlet to purge contaminated air inside an aircraft.

In another specific embodiment, the air supply system is a zeolite-type oxygen generator.

In accordance with another embodiment, the present disclosure provides an aircraft having an airframe, including a fuselage having an interior, configured to accommodate at least one occupant. The aircraft includes an air supply system, configured to direct oxygenated air to the at least one occupant, and a monitor of a condition of air in the air supply system. A backup oxygen supply is provided, and a controller is configured to activate the backup oxygen supply when the monitor detects a failure of the air supply system.

In accordance with yet another embodiment, the present disclosure provides a method for providing breathable air to an occupant of an aircraft. The method includes the steps of providing air to the at least one occupant from an air supply, monitoring a condition of the air, and automatically activating a backup oxygen supply upon detection of a failure of the air supply.

The features, functions and advantages that have been discussed can be achieved independently in various embodiments or may be combined in yet other embodiments, further details of which can be seen with reference to the following description and drawings.

BRIEF DESCRIPTION OF THE DRAWINGS

The drawings described herein are for illustration purposes only and are not intended to limit the scope of the present disclosure in any way.

DETAILED DESCRIPTION

Illustrative embodiments are described below as they might be employed in an on-board oxygen generating system. In the interest of clarity, not all features of an actual implementation are described in this specification. It will of course be appreciated that in the development of any such actual embodiment, numerous implementation-specific decisions must be made to achieve the developers' specific goals, such as compliance with system-related, regulation-related and/or business-related constraints, which will vary from one implementation to another. Moreover, it will be appreciated that such a development effort might be complex and time-consuming, but would nevertheless be a routine undertaking for those of ordinary skill in the art having the benefit of this disclosure.

Further aspects and advantages of the various embodiments will become apparent from consideration of the following description and drawings. These embodiments are described in sufficient detail to enable those skilled in the art to practice the invention, and it is to be understood that modifications to the various disclosed embodiments can be made, and other embodiments can be utilized, without departing from the spirit and scope of the present invention. The following detailed description is, therefore, not to be taken in a limiting sense.

Figure 1:
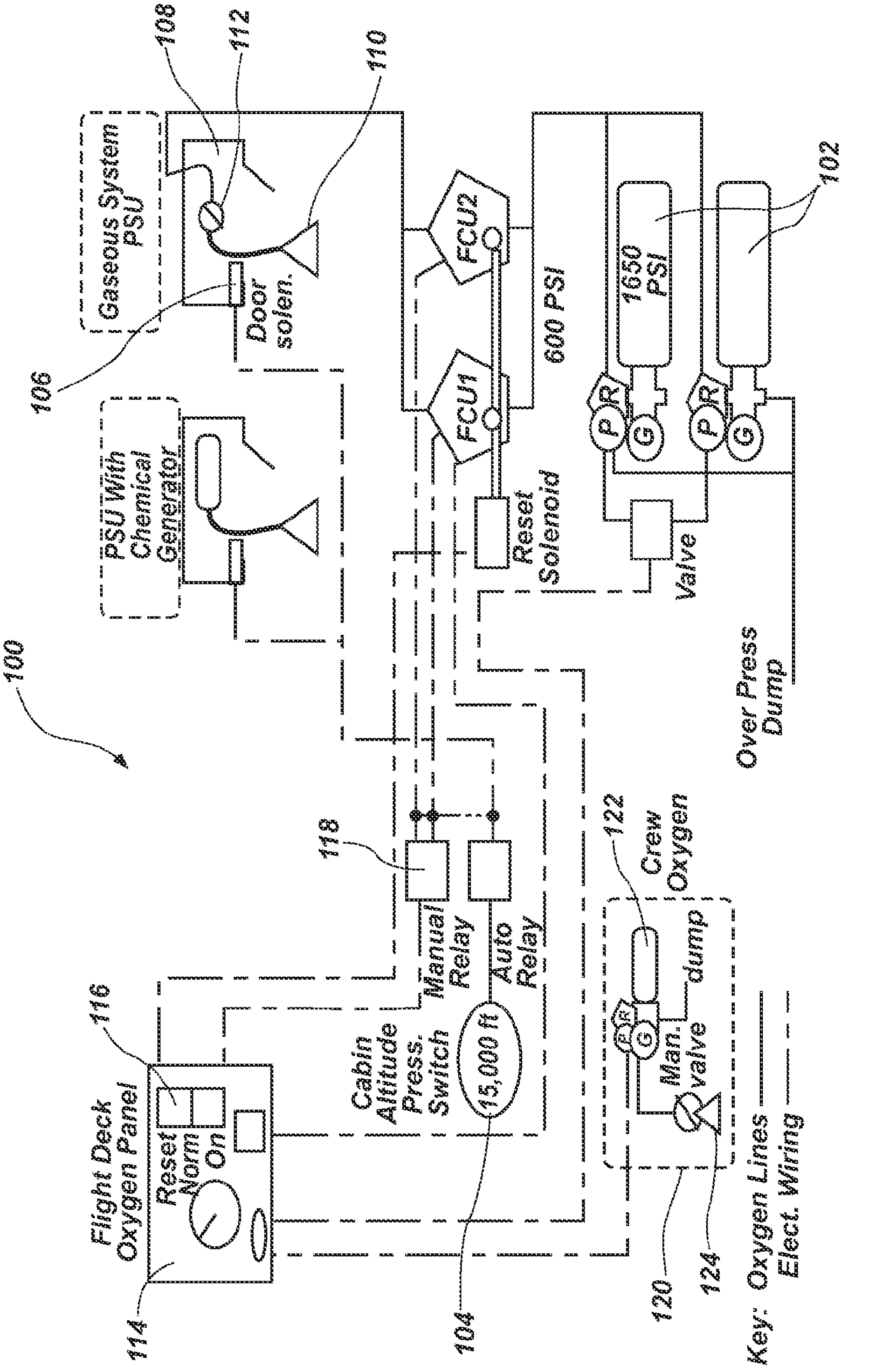
FIG. 1 is a schematic diagram of a prior art emergency oxygen system for an aircraft using bottled oxygen.

Shown in FIG. 1 is a schematic diagram of a prior art aircraft emergency oxygen system 100 using bottled oxygen. This system includes cylinders 102 of compressed or liquid oxygen that can be activated to provide oxygen to the passengers and crew in case of high altitude decompression or smoke, etc. in the cabin or cockpit. Specifically, the system 100 includes a cabin altitude pressure switch 104 that automatically activates the emergency oxygen system in case of cabin decompression. When decompression is detected, the cabin altitude pressure switch 104 automatically sends a signal to a door latch device 106 on each passenger service unit 108, which allows the oxygen mask(s) 110 therein to drop for use by a passenger. When the passenger pulls on the oxygen mask 110, this rotates a valve 112, which allows oxygen to flow to the mask.

The oxygen to the oxygen mask(s) 110 is provided from the oxygen cylinders 102, which are connected via suitable pressure sensors, regulators, gauges and valves to provide oxygen to a main oxygen supply line that extends to each passenger service unit 108. Each oxygen mask 110 can be provided with a vacuum sensor (not shown in FIG. 1) to detect inhaling by a user, so that the system can provide pulse-demand oxygen for the user, rather than a constant flow, which could waste the finite oxygen supply.

The bottled oxygen system 100 shown in FIG. 1 also includes a flight deck control panel 114, through which the flight crew can control the system. This includes a manual activation switch 116, connected to a manual relay 118, by which the flight crew can activate the emergency oxygen system at will. In the embodiment of FIG. 1, the crew oxygen system 120 includes its own oxygen supply bottle 122, which feeds oxygen to an oxygen mask 124 for each crew member, in a manner similar to that discussed above. Other features and details of typical aircraft emergency oxygen supply systems and how they operate will be known to those of skill in the art.

In the system 100 of FIG. 1, so long as the oxygen in the bottles 102 and 122 is pure, there is essentially no way for the oxygen system 100 to become contaminated. Thus, air sensors are typically not provided in the emergency oxygen system 100, because they are considered unnecessary. Unfortunately, however, bottled oxygen systems are considered to present reliability, safety and maintenance issues. In addition, stored-gas systems have capacity limitations, since compressed oxygen bottles necessarily contain a finite supply. In response to these issues regarding bottled oxygen systems, on-board oxygen generating systems have been developed.

Figure 2:
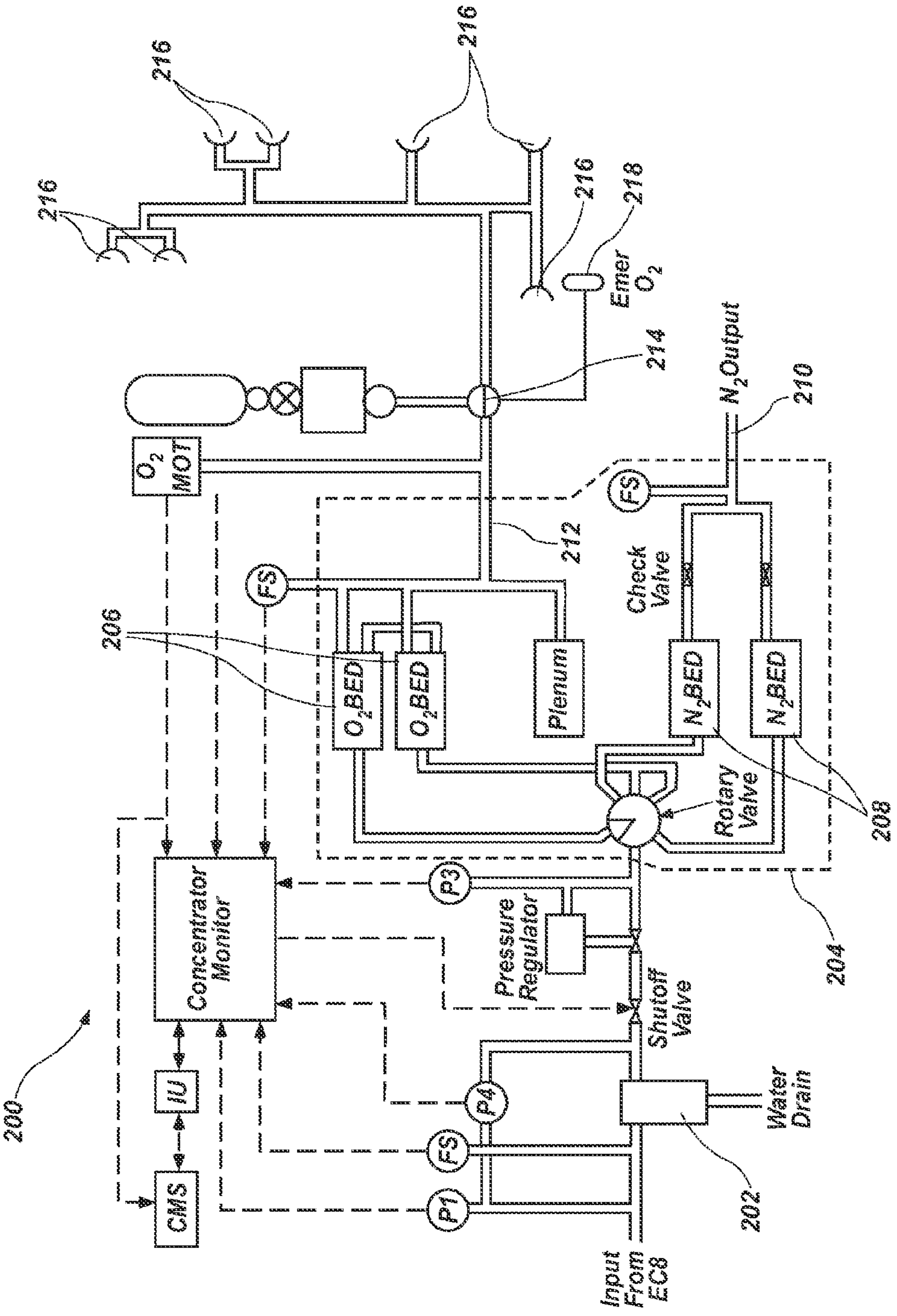
FIG. 2 is a schematic diagram of a prior art on-board oxygen generating system with an emergency oxygen bottle.

A schematic diagram of one type of on-board oxygen generation and oxygen supply system 200 for a commercial aircraft is shown in FIG. 2. In this embodiment, air from outside the aircraft is compressed by an aircraft engine or other device (e.g. an APU, compressor, supercharger, etc.), and typically passed through a heat exchanger (not shown), to ensure that the air is at a suitable temperature, and a water separator 202 on its way to the OBOGS device 204. The OBOGS device 204 uses an adsorbent to remove nitrogen from the compressed air, which consequently enriches the oxygen concentration in the air stream. In the embodiment shown in FIG. 2, the oxygen concentrating units 206 are labeled "$O_2$ Bed." Materials such as zeolite are commonly used as absorbents in an OBOGS to remove nitrogen and concentrate oxygen. These materials are often produced as small crystallites, bound with clay or an organic polymer to form small beads. Various aspects and features of commercially-available nitrogen absorption systems will be understood by those of skill in the art. The nitrogen that is removed from the air stream by the oxygen concentrating units 206 is routed to nitrogen units 208 and can be eliminated through an exhaust conduit 210.

The system 200 in FIG. 2 shows an emergency oxygen system for an aircraft crew only. However, it is to be understood that a single OBOGS system can provide oxygen for both the crew and passengers of an aircraft, or multiple OBOGS units can be used in a single aircraft, dedicated to use in different parts of the aircraft, such as one unit for the cockpit, and separate unit(s) that supply oxygen for the cabin. Other combinations can also be used. In the system 200 of FIG. 2, an oxygen outlet conduit 212 directs oxygenated air from the oxygen concentrating units 206 through a selector valve 214 to a plurality of oxygen masks 216 for the crew.

A backup oxygen supply is also provided in the system 200 of FIG. 2, in the form of an oxygen bottle 218, which is connected to the selector valve 214. Unfortunately, the selector valve is a manual valve, and requires specific action by the crew to switch over from the OBOGS device 204 to the backup oxygen. Additionally, the system 200 of FIG. 2 does not detect or provide any warning to the crew regarding a variety of potential malfunctions or danger conditions with the primary oxygen system, such as carbon monoxide, inadequate flow rate, hydrocarbons in the oxygen stream, etc. Some of these conditions may not be readily noticeable by the crew.

Figure 3:
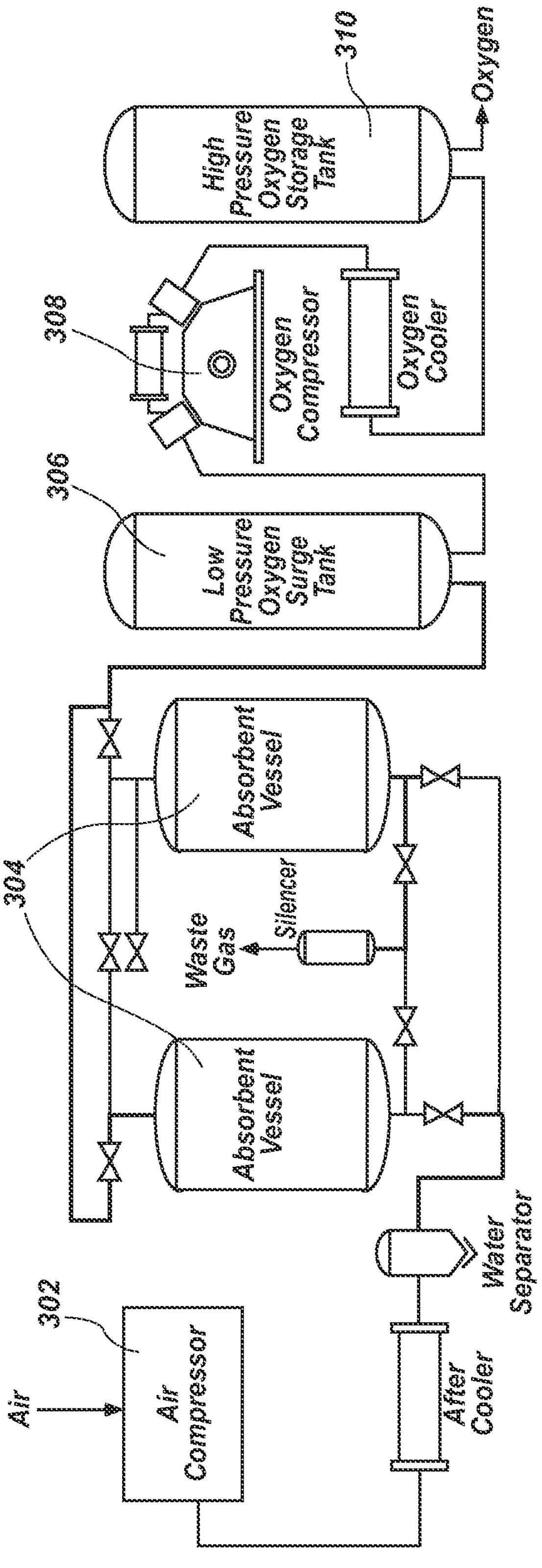
FIG. 3 is a schematic diagram of a prior art on-board oxygen generating system with no air quality sensor or backup oxygen supply.

Another OBOGS system 300 is shown in FIG. 3. This system 300 includes a compressor 302 or similar device that draws in atmospheric air for compression, after which the air passes through one of two absorbent vessels 304 that absorb nitrogen and concentrate oxygen. This compressed oxygenated air then travels to a low pressure oxygen surge tank 306, thence through an oxygen compressor 308 and to a high pressure oxygen storage tank 310. It is from this high pressure storage tank that oxygen is provided to the passengers and crew, in the manner mentioned above. Once again, with this system there is no backup oxygen supply.

Figure 4:
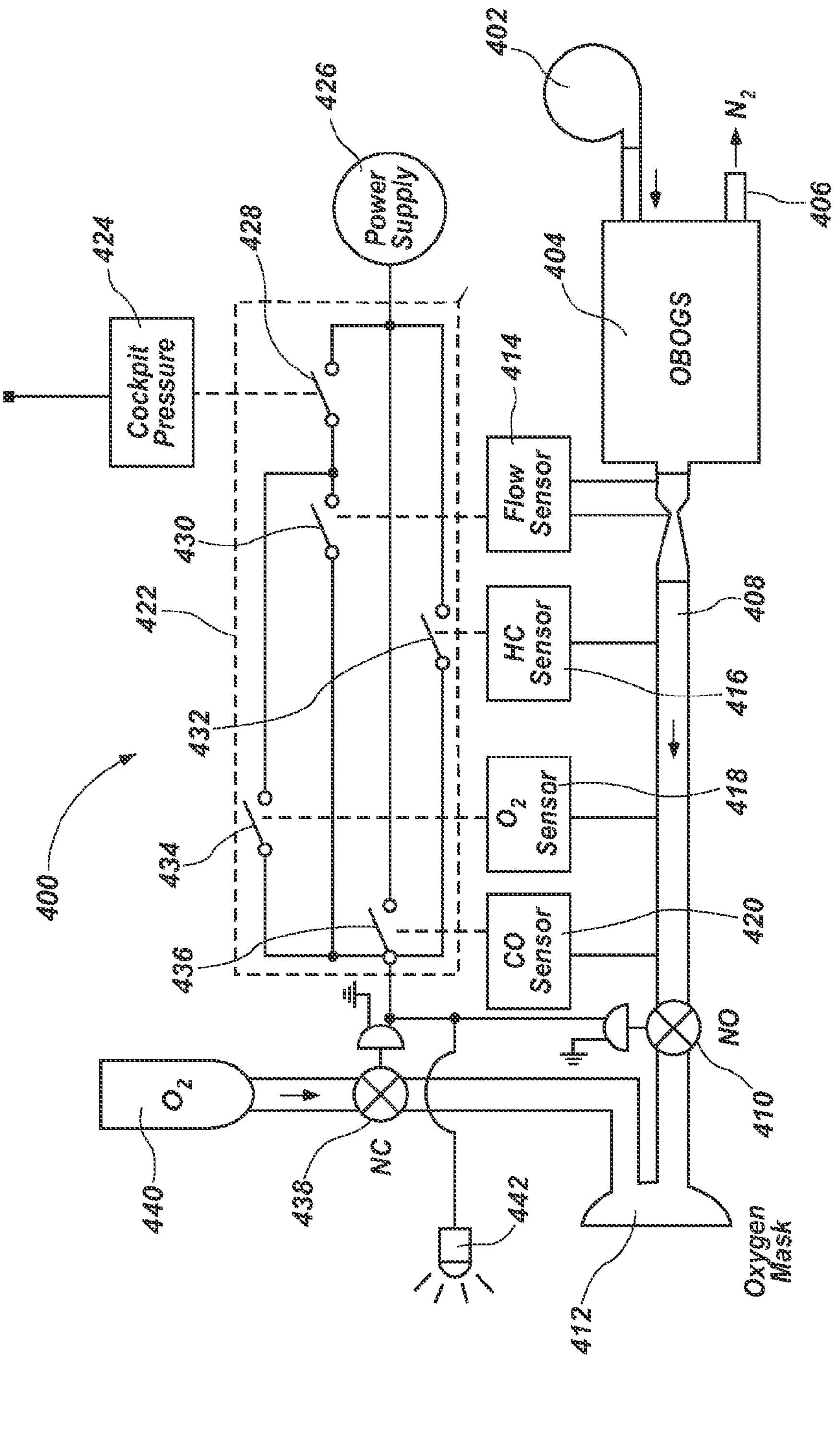
FIG. 4 is a schematic diagram of an embodiment of an automatic on-board oxygen-generating backup system with control logic.

Advantageously, the present disclosure provides an onboard oxygen-generating system for an aircraft that addresses some of the issues mentioned above with respect to the embodiments of FIGS. 1-3. The system disclosed herein monitors contaminant levels in the air supply, provides a pristine independent oxygen backup, and provides emergency air supply for purging. One embodiment of such a system is shown in FIG. 4. It is to be understood that the various embodiments of an oxygen generation system shown herein do not necessarily show all the components of such a system, such as flow regulators, pressure sensors, check valves, water separators, etc., as well as the operational and control devices that are normally part of aircraft emergency oxygen systems. However, those of skill in the art will be aware of the many routine components that are included as part of such systems, and will be able to configure operating systems that incorporate the features disclosed herein.

The system 400 of FIG. 4 generally includes a compressed air source 402, which is represented in this figure as a pump, and which provides compressed air to an OBOGS device 404, which absorbs nitrogen and concentrates oxygen. As discussed above, the compressed air source can be an engine bleed connection, APU, etc. Other related devices, such as a heat exchanger, valves, etc., are not shown in this figure, but will be understood by those of skill in the art. Oxygen generating systems are commercially available from a variety of sources, and can provide a range of performance characteristics, as will be understood by those of skill in the art. One commercial supplier of oxygen generating systems is Cobham Life Support of Davenport, Iowa, U.S.A., which markets an oxygen generating system that takes a 25 psig input pressure, and can provide up to 60 LPM of oxygen at concentrations of from 50% to about 95% oxygen, depending on the output flow rate between 20 and 60 LPM and the measured altitude.

The OBOGS 404 includes a nitrogen exhaust conduit 406 and an oxygen outlet conduit 408. The outlet conduit passes through a first valve 410, which is normally open ("NO"), to an oxygen mask 412 that can be worn by a passenger or crew member to receive the oxygen supply. Positioned along the outlet conduit 408 are a plurality of sensors, which are associated with an OBOGS monitor, as disclosed herein. These sensors include a flow sensor 414, a hydrocarbon sensor 416, an oxygen ($O_2$) sensor 418 and a carbon monoxide (CO) sensor 420. The flow sensor 414 detects (e.g. via a Venturi tube) whether the gas flow rate from the OBOGS is within a desired range. The hydrocarbon sensor 416 detects the presence of free hydrocarbons in the OBOGS outflow, such as propane and other partial combustion products. Such hydrocarbons can be indicative of conditions such as smoke, oil leakage from the engine or APU, engine or APU failure, etc. Finally, the oxygen sensor 418 detects the concentration of oxygen in the OBOGS outflow, and the CO sensor 420 detects the presence of carbon monoxide, which can also be indicative of failure of the engine or APU, or other malfunction. It is to be understood that the specific group of sensors shown in FIG. 4 is exemplary only. A different quantity and variety of sensors can be used in a system configured in accordance with this disclosure.

The sensor group is connected to an OBOGS monitor 422, which is represented as a series of switches in FIG. 4, and receives electrical power from an electrical power supply 426. In addition to the group of sensors positioned along the OBOGS outlet 408, a cockpit or cabin pressure sensor 424 can also be connected to the monitor 422. While the monitor is depicted as a group of switches, its functions can be performed by any suitable combination of hardware, software, integrated circuits, discrete electrical components, etc.

Closure of any of the switches shown in the monitor 422 will cause valve 410 to close, and valve 438, which is normally closed ("NC") and connects to a backup oxygen supply 440, to open. This cuts-off or blocks air from the OBOGS to the wearer's mask 412, and opens the backup oxygen supply 440 to the individual. In this way, the system 400 automatically blocks the flow from the standard emergency oxygen supply system, and switches to an uncontaminated oxygen supply in case of any one of a variety of problems with the OBOGS system. The valves 410 and 438 can be solenoid actuated valves, for example, and the backup oxygen supply can be provided from a pre-charged canister or tank/bottle, chemical oxygen generator, or other suitable device. The backup oxygen supply 440 is shown connected to the mask with a separate flow conduit from the conduit 408. Alternatively, the conduit from the backup oxygen supply 440 can connect to the flow conduit 408 at some position downstream of the first valve 410. In such a configuration, after closure of the first valve 410 and opening of the backup oxygen valve 438, the pure oxygen supply will purge any remaining air from the conduit 408 to the mask 412. In this way, the backup oxygen supply 440 provides a supply for purging the emergency air system when there is a malfunction.

The control logic of the monitor 422 is evident through analysis of the switches shown in FIG. 4. Through the pressure sensor 424, the system 400 first monitors cabin or cockpit altitude. Switch 428 is normally open when adequate pressure is detected in the cabin or cockpit. This is to be expected when the aircraft and the cabin or cockpit ventilation and pressurization system are working properly, or when the aircraft is at low altitude, and no oxygen is needed. However, if the cabin or cockpit pressure drops below a certain level, switch 428 will close, allowing the air monitor 422 to operate. This condition will correspond to any situation in which the OBOGS device operates. For military aircraft, in which the crew always wears an oxygen mask at higher altitude, this will be substantially the entire time the aircraft is at high altitude. For commercial aircraft, this will correspond to any situation in which there is a need for emergency oxygen.

When the switch 428 is closed, the closing of any other switch in the monitor 422 (i.e. when contaminated air is sensed), will cause the valves 410 and 438 to close and open, respectively, allowing the backup oxygen supply 440 to flow to the mask 412. For example, if the flow sensor 414 detects an abnormal flow from the OBOGS device 404, switch 430 will close, causing the monitor to trigger valves 410 and 438, thus switching the oxygen supply from the OBOGS 404 to the pure oxygen supply 440. The same is true of the other sensors. If any of the hydrocarbon sensor 416, $O_2$ sensor 418 or CO sensor 420 are triggered, indicating a malfunction or compromised condition of the oxygen from the OBOGS 404, the corresponding switches 432, 434 and 436 will close, respectively, thus switching the flow from the OBOGS 404 to the backup supply 440. Each sensor in the group of sensors thus detects a triggering condition that will cause the oxygen source to switch from the OBOGS 404 to the backup oxygen supply 440, whenever the cockpit pressure sensor switch 428 is closed. In this way, the system 400 automatically switches to a backup supply whenever needed. It is to be appreciated that where other types of sensors are used, these can present other triggering conditions for the automatic switch to the backup oxygen supply.

The system 400 can also include a bad air supply warning 442 (e.g. a warning light or other indicator), that automatically notifies the crew of a failure in the OBOGS device 404. In the embodiment shown in FIG. 4, this warning indicator 442 is connected to the electrical connection from the monitor 422 to the valves 410, 438, so that it illuminates only when the monitor triggers the valves to switch to the backup oxygen supply. Alternatively, the bad air supply warning can be connected to any or all of the sensors 414-420 to provide the crew with a direct indication of conditions of the oxygen supply that could arise from several causes with several scenarios. Other alternatives can also be used for a bad air supply warning that is cognizable by a user of the system.

The oxygen system 400 shown in FIG. 4 is depicted with a single oxygen mask 412. However, this is for simplicity in representation only. This same system 400 and control logic can also be applied to an automatic OBOGS for an aircraft having multiple oxygen supply masks for passengers, crew, etc. The same is true with other embodiments shown herein.

Figure 5:
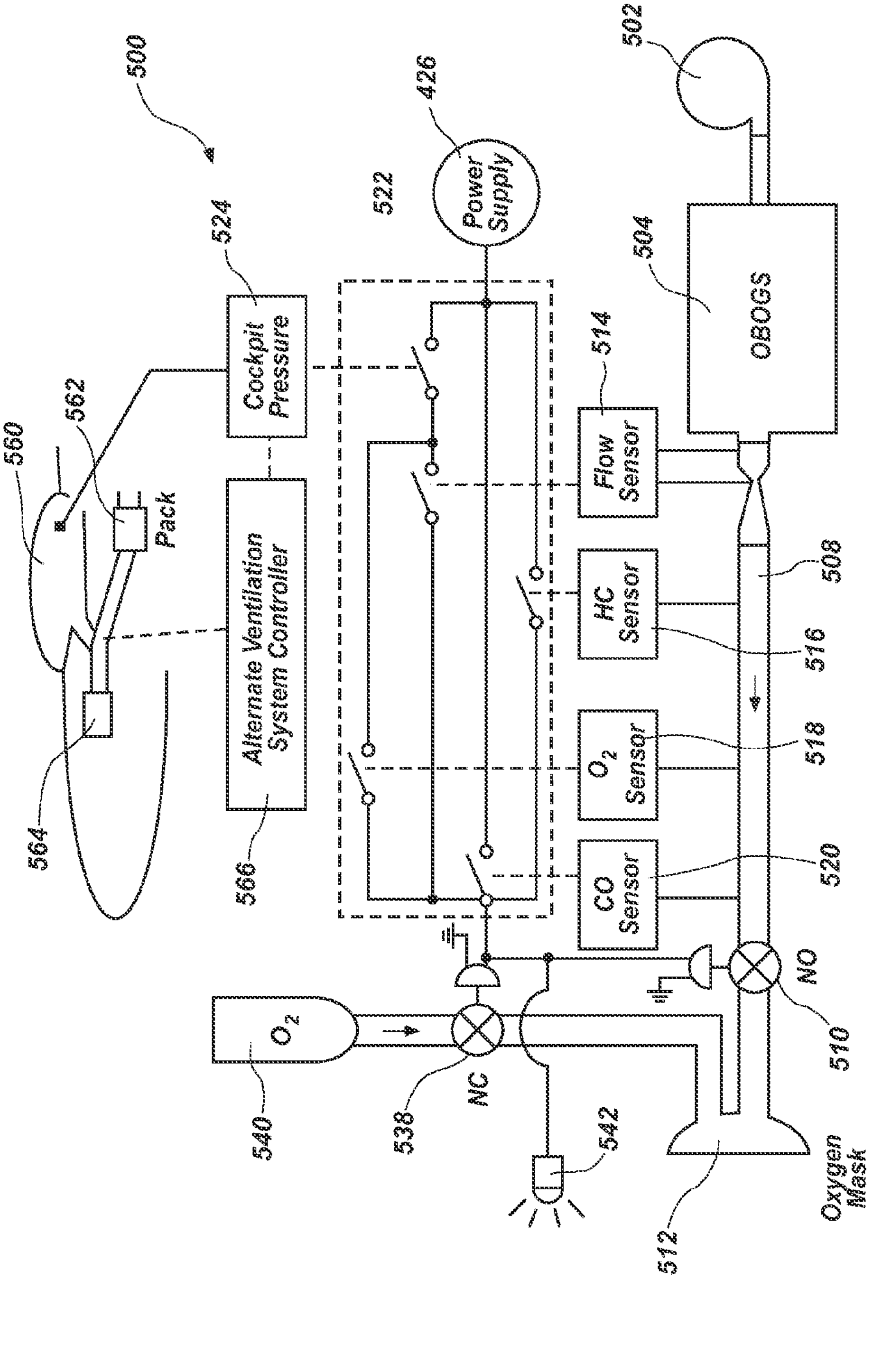
FIG. 5 is a schematic diagram of another embodiment of an automatic on-board oxygen generating system with backup oxygen and an alternate ventilation system.

Another embodiment of an automatic on-board oxygen generating system is shown in FIG. 5. This system 500 is like that shown in FIG. 4, and includes an OBOGS device 504 with an oxygen outlet conduit 508 and a plurality of sensors 514-520 disposed along that conduit. The sensor group is connected to an OBOGS monitor 522, which is also connected to a cockpit or cabin pressure sensor 524. The monitor 522 is configured to cause valve 510, which normally open, to close. The monitor 522 is also configured to cause valve 538, which is normally closed and connects to a backup oxygen supply 540, to open whenever the cockpit altitude is above a certain level and any of the sensors detects a triggering condition, as discussed above. This cuts-off the OBOGS flow to the wearer's mask 512, and opens the backup oxygen supply 540 to the individual. In this way, the system 500 automatically switches to an uncontaminated oxygen supply in case of any one of a variety of problems with the OBOGS device 504.

The system 500 can also include a bad air supply warning 542 that automatically notifies the crew of a failure in connection with the OBOGS device 504, as discussed above. Though not shown in FIG. 5, this embodiment can also include an exhaust conduit for eliminating or venting $N_2$ from the OBOGS device 504, and can either vent the $N_2$ to the atmosphere or communicate with a fuel inerting system, as discussed below with respect to the embodiments of FIGS. 7 and 8.

The embodiment of FIG. 5 also includes an alternate ventilation system. In this embodiment, the aircraft 560 includes a cockpit air cycle machine 562 that is connected to a ram air inlet 564. The cockpit air cycle machine 562, also referred to as a cockpit air pack, is part of the cockpit heating and ventilation system. These components together are part of the aircraft environmental control system (ECS), and are well known. The cockpit air cycle machine 562 can include a heat exchanger and compressor, and operates to compress and cool air, and cool aircraft electronics. The cockpit air cycle machine 562 and ram air inlet 554 are associated with an alternate ventilation system controller 566, which is operationally interconnected with the cockpit pressure sensor 524. While the embodiment of FIG. 5 is depicted in the context of a military aircraft, this embodiment can also be applied to larger aircraft, in which the heating and ventilation system and ram air inlet also provides passenger cabin air flow.

In case of emergency, such as depressurization, smoke, etc., the ram air inlet 564 can be opened, allowing fresh air to enter the aircraft 560 and be at least partially pressurized by the forward velocity of the aircraft. Vents that allow contaminated air to flow out of the cabin will normally be open. If ram pressure and ambient pressure are sufficient to maintain a marginal minimum pressure within the aircraft, e.g. 6.7 psia (20,000 ft cockpit altitude), then the ECS ram inlet 564 can be opened to the cockpit, to purge contaminated air that was delivered by a failed OBOGS unit or air supply.

Figure 6:
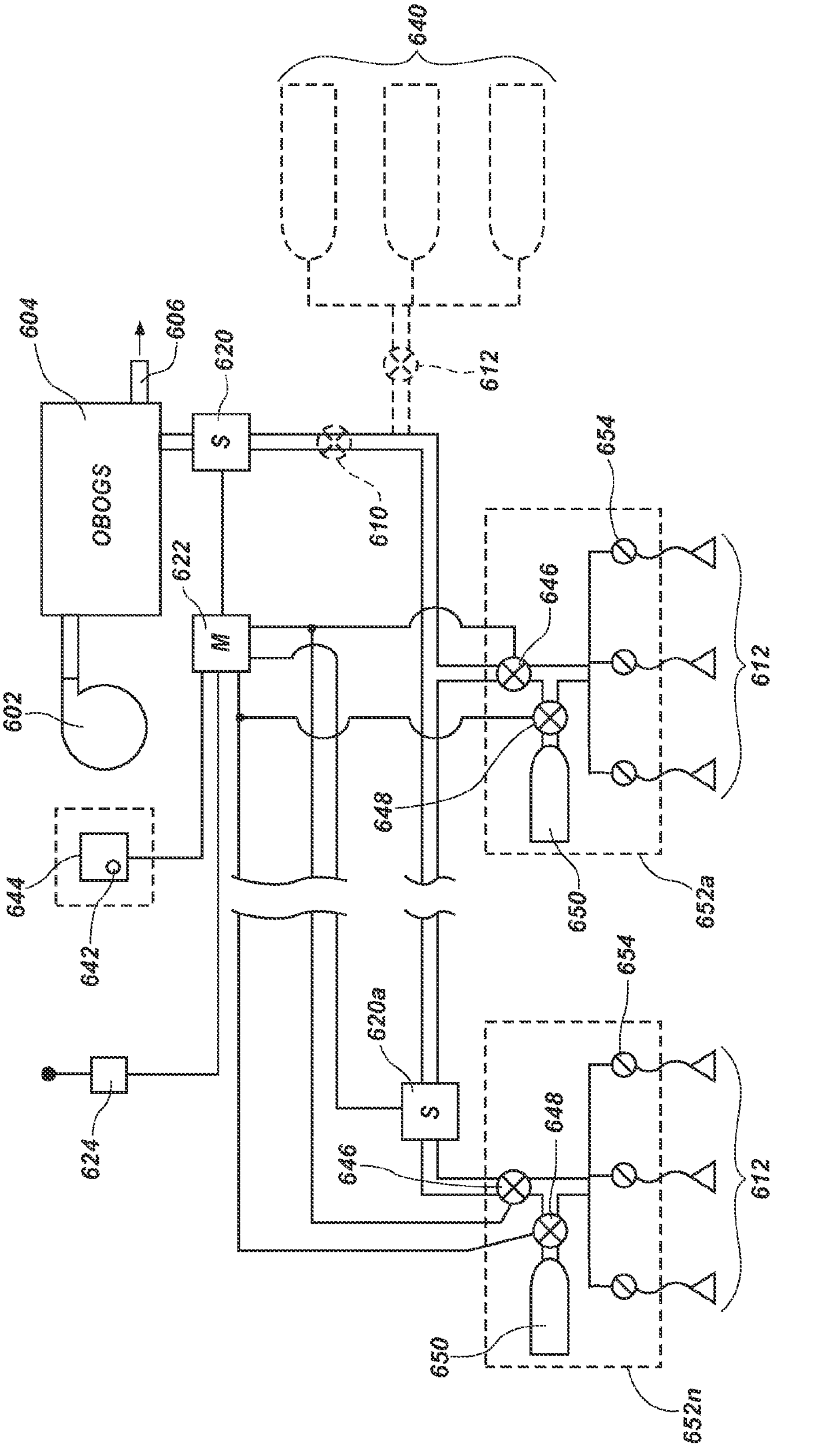
FIG. 6 is a schematic diagram showing an embodiment of an automatic on-board oxygen-generating backup system with control logic in accordance with the present disclosure, configured to provide emergency oxygen for a passenger cabin of an aircraft.

As noted above, though they are shown with just a single oxygen mask, the embodiments shown in FIGS. 4 and 5 can be applied to a system that provides oxygen to multiple oxygen masks, such as for passengers in a commercial aircraft. A schematic diagram of an embodiment of an automatic OBOGS with backup oxygen in accordance with the present disclosure, configured to provide emergency oxygen for multiple passengers in a passenger cabin of an aircraft, is shown in FIG. 6. This system 600 includes the functional elements of the embodiment of FIG. 4, including a pressurized air source 602, which provides pressurized air to an OBOGS device 604, having an exhaust conduit 606 and an oxygen outlet conduit 608. Air from the OBOGS device 604 initially passes through a sensor unit 620, which can include an array of sensors (e.g. sensors for flow, hydrocarbons, $O_2$, CO, etc., as discussed above) that detect characteristics of the OBOGS outflow.

The sensor unit 620 is connected to a monitor device 622, which can receive signals from the sensor unit 620 and from a pressure sensor 624, and operates according to the control logic discussed above. The monitor 622 can be connected to a cockpit control panel 644, which can include an indicator light 642 or other device for providing a cognizable signal of operation of the system to a crew member, etc. It is to be understood that, while the monitor 622 is shown as a unit that is separate from the sensor array 620 in FIG. 6, the monitor 622 can alternatively be combined with the sensor array 620, or it can be combined with other devices in an aircraft, and it can be positioned in a variety of locations in the aircraft, such as in the cockpit, or near the OBOGS device, or elsewhere. Moreover, the functions of the monitor 622 can be programmed as part of any suitable computing device with a processor and system memory, whether that device is a special purpose device or an on-board computer that controls a variety of aircraft systems. Likewise, the sensor array 620 can be a single device with one or more sensors, or a plurality of separate sensor devices can be used to monitor the outflow an OBOGS device, and the actual placement of these devices can vary. The wide array of alternatives for the placement and configuration of the monitor and the sensors applies to all embodiments herein that include these features.

The embodiment shown in FIG. 6 shows two alternative ways in which backup oxygen can be provided to passengers. The oxygen conduit 608 from the OBOGS device 604 extends to a series of passenger service units (PSU's) 652*a* . . . 652*n*, etc., to provide oxygen to a plurality of oxygen masks 612 that are stowed in the PSU's. As is well known, in case of cabin depressurization or other emergency, doors on the PSU's open, allowing the oxygen masks 612 to drop down for use by the passengers. When oxygen masks deploy for passengers, the OBOGS device 604 will be operating, sending oxygen to each PSU 652. A user of an individual mask 612 pulls on the tubing of their mask, which opens a valve 654 to allow oxygen to flow to that mask. Those of skill in the art will be aware that aircraft OBOGS devices can operate at different output levels, so that the OBOGS device can increase or decrease its output depending on the demand.

In one embodiment, shown in FIG. 6, each PSU 652 includes an oxygen master valve 646, a backup oxygen valve 648 and a small backup oxygen supply bottle 650. The oxygen master valve 646 is normally open and communicates with the oxygen supply conduit 608. The backup oxygen valve 648 is normally closed, and communicates with the backup oxygen supply bottle 650. When the monitor 622 detects a triggering condition of the output of the OBOGS in line 608 (based on signals from the sensor array 620), the monitor 622 automatically sends a signal that closes each oxygen master valve 646, to block air from the oxygen generating device 604, and opens each backup oxygen valve 648. In this way, the system 600 automatically switches to pure oxygen in case of a malfunction of the emergency OBOGS, as discussed above, and uses a small volume oxygen supply that is positioned in each PSU 652. When this switch is made, from one oxygen source to another, a signal can also be sent to the indicator light 642 or other crew alert device, alerting the aircrew to the OBOGS condition.

As an alternative to a separate oxygen supply bottle in each PSU 652, a single backup oxygen supply can be provided in the form of larger oxygen bottles 640. This alternate embodiment is also shown in dashed lines in FIG. 6. In this embodiment, a first valve 610 is positioned in the oxygen conduit 608, and is normally open. A backup oxygen valve 612 is associated with the single backup oxygen supply 640, and is normally closed. When a triggering condition is detected by the sensor array 620, the monitor 622 automatically sends a signal that closes the first valve 610 block air from the oxygen generating device 604, and opens the backup oxygen valve 612.

With a single backup oxygen supply 640 and a single pair of valves 610, 612, rather than separate valves and separate backup oxygen in each PSU 652, this latter alternative arrangement presents fewer components and thus fewer points for possible malfunction. On the other hand, this alternative arrangement also places the oxygen supply line shutoff valve 610 farther from each oxygen mask 612. The result of this arrangement is that upon switching to the backup oxygen, a larger volume of air in the oxygen supply pipe 608 will flow out before the pure oxygen from the backup supply takes over. If the air in the oxygen supply conduit 608 is contaminated, this arrangement will thus involve more pure air to purge the system 600 before the pure oxygen is received by users of a mask 612. In order to assure that the oxygen line 608 is properly purged in such a situation, a second sensor device 620*a* can be provided at or near the most distant PSU 652*n*, in order to send a signal to the monitor 622 to indicate when the oxygen system has been satisfactorily purged. This system 600 thus automatically switches to pure oxygen in case of a malfunction of the emergency OBOGS, as discussed above, and uses a larger volume oxygen supply that can be positioned in a central location in the aircraft. It will be apparent that multiple central oxygen supplies can also be used, such as one for each section of an aircraft cabin, or one for each seating group of a seat row.

The embodiments of FIGS. 3-6 each include an exhaust conduit (e.g. exhaust conduit 406 in FIG. 4) for venting $N_2$ from the OBOGS device. Nitrogen is a byproduct of oxygen generation using absorption-type oxygen generators. Those of skill in the art will be aware that many aircraft also include fuel inerting systems, which involve on-board inert gas generation systems (OBIGGS) to generate nitrogen for filling the head space of fuel tanks (to reduce the likelihood of combustion). Many of these systems produce oxygen as a byproduct. Thus it has been recognized that on-board oxygen and nitrogen generation devices can have dual uses, producing oxygen for passengers and nitrogen for fuel inerting.

Figure 7:
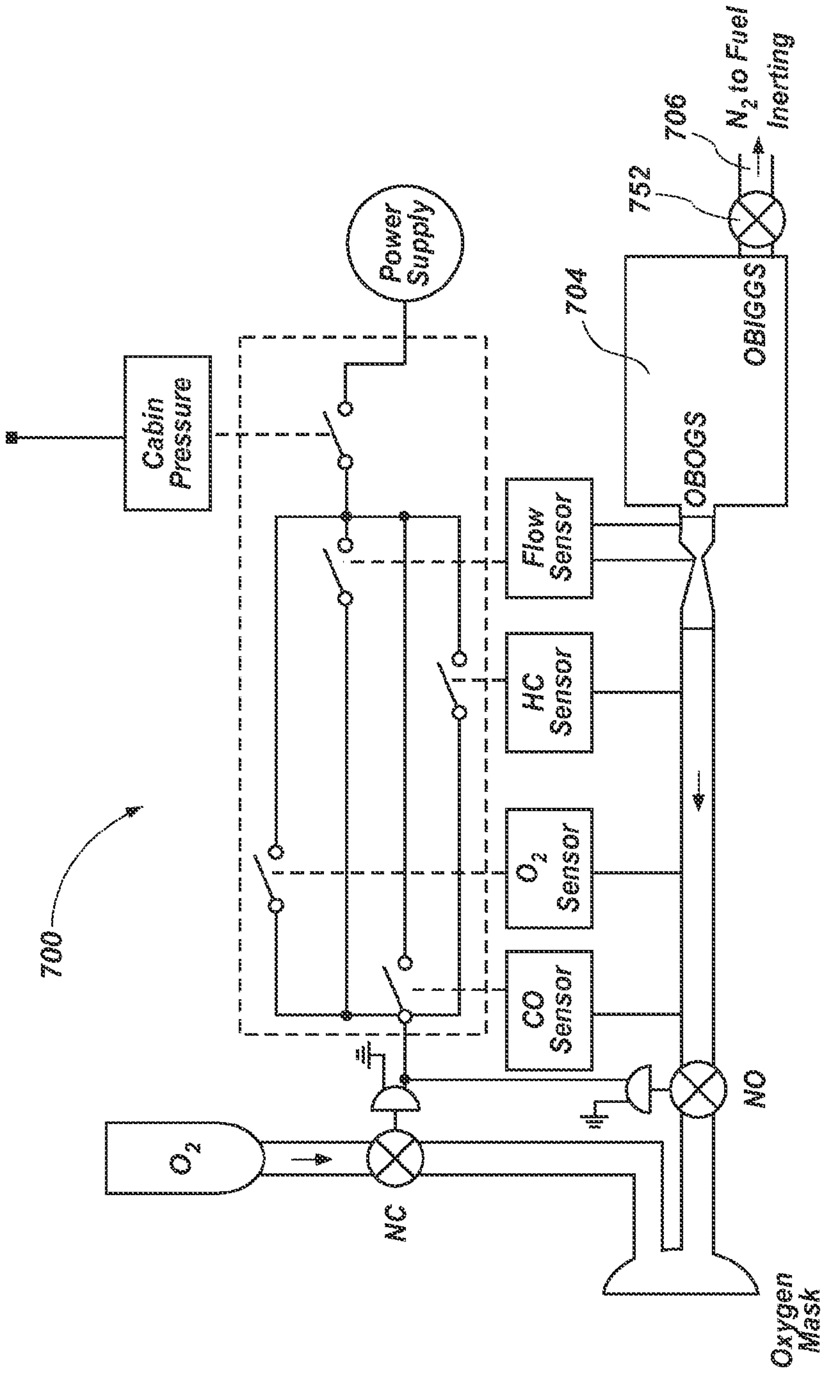
FIG. 7 is a schematic diagram of an embodiment of an automatic on-board oxygen-generating system using oxygen from an on-board inert gas generating system.

Shown in FIG. 7 is an embodiment of an on-board oxygen generating system 700 with a connection to a fuel inerting system. This embodiment is substantially like that of FIG. 4, and the common elements will not be described here. Advantageously, in this embodiment the exhaust conduit 706 for eliminating or venting $N_2$ from the OBOGS device 704 includes a check valve 752, and leads to a fuel inerting system (not shown). At the same time, the oxygen produced by the OBOGS device 704 can be provided for emergency oxygen, as discussed above. Thus, the OBOGS device 704 is also an OBIGGS device.

Another embodiment of an on-board oxygen generation system with a connection to a fuel inerting system is shown in FIG. 8. Like the embodiment discussed above, this system 800 includes an OBOGS device 804 which receives compressed air from a compressed air source (e.g. engine, APU, etc., not shown), in the manner discussed above. The OBOGS device 804 includes a nitrogen exhaust conduit 806 and at least one oxygen outlet conduit 808. Disposed along the oxygen outlet conduit 808 are a plurality of sensors, such as a hydrocarbon sensor 816, $O_2$ sensor 818 and CO sensor 820. These sensors are connected to an OBOGS monitor 822, which receives electrical power from an electrical power supply 826. In addition to the group of sensors positioned along the OBOGS outlet 808, a cockpit or cabin pressure sensor 824 is also connected to the monitor 822. As with the embodiment of FIG. 4, the monitor is depicted as a group of switches, which represent its control logic, though its functions can be performed by any suitable combination of hardware, software, integrated circuits, discrete electrical components, etc.

The OBOGS device 804 is connected to the aircraft cabin via the conduit 808, which passes through the power-actuated valve 810, which is normally open. During normal operation, the OBOGS device 804 provides oxygen to the cabin to help reduce hypoxia. This oxygen can be mixed into the normal cabin ventilation system. As will be appreciated by those of skill in the art, even though an aircraft cabin is pressurized to a breathable cabin altitude (e.g. 8,000 ft.), some passengers can experience discomfort with mild hypoxia at that pressure level. Thus, it can be desirable to provide additional oxygen for passengers, to relieve this discomfort and enhance crew productivity, even at the standard cabin pressure. As discussed above, since some aircraft that are equipped with an OBIGGS and a fuel inerting system can naturally produce oxygen as a byproduct, this oxygen can be used for this purpose.

However, as with the embodiments discussed above, when the cabin pressure sensor 824 indicates a low pressure reading, and any one of the sensors 816-820 are also triggered by some triggering event (e.g. detected CO, hydrocarbons, or low $O_2$), the triggering event will be detected by the monitor 822, which will cause the valve 810 to close, thus blocking air flow from the OBOGS device 804, and preventing contaminants from being introduced into the cabin air.

Figure 8A:
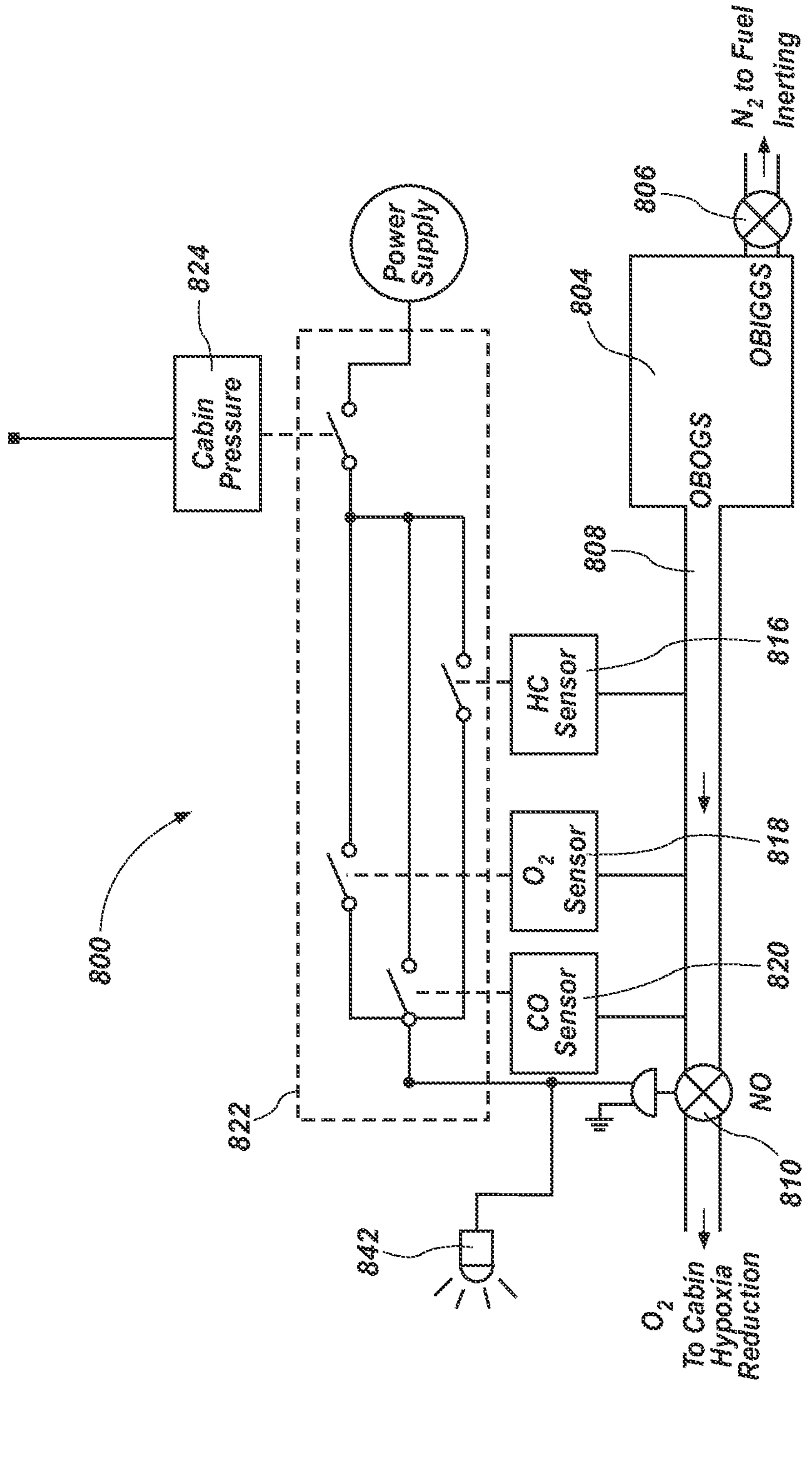
FIG. 8A is a schematic diagram of another embodiment of an automatic on-board oxygen-generating system using oxygen from an on-board inert gas generating system.
Figure 8B:
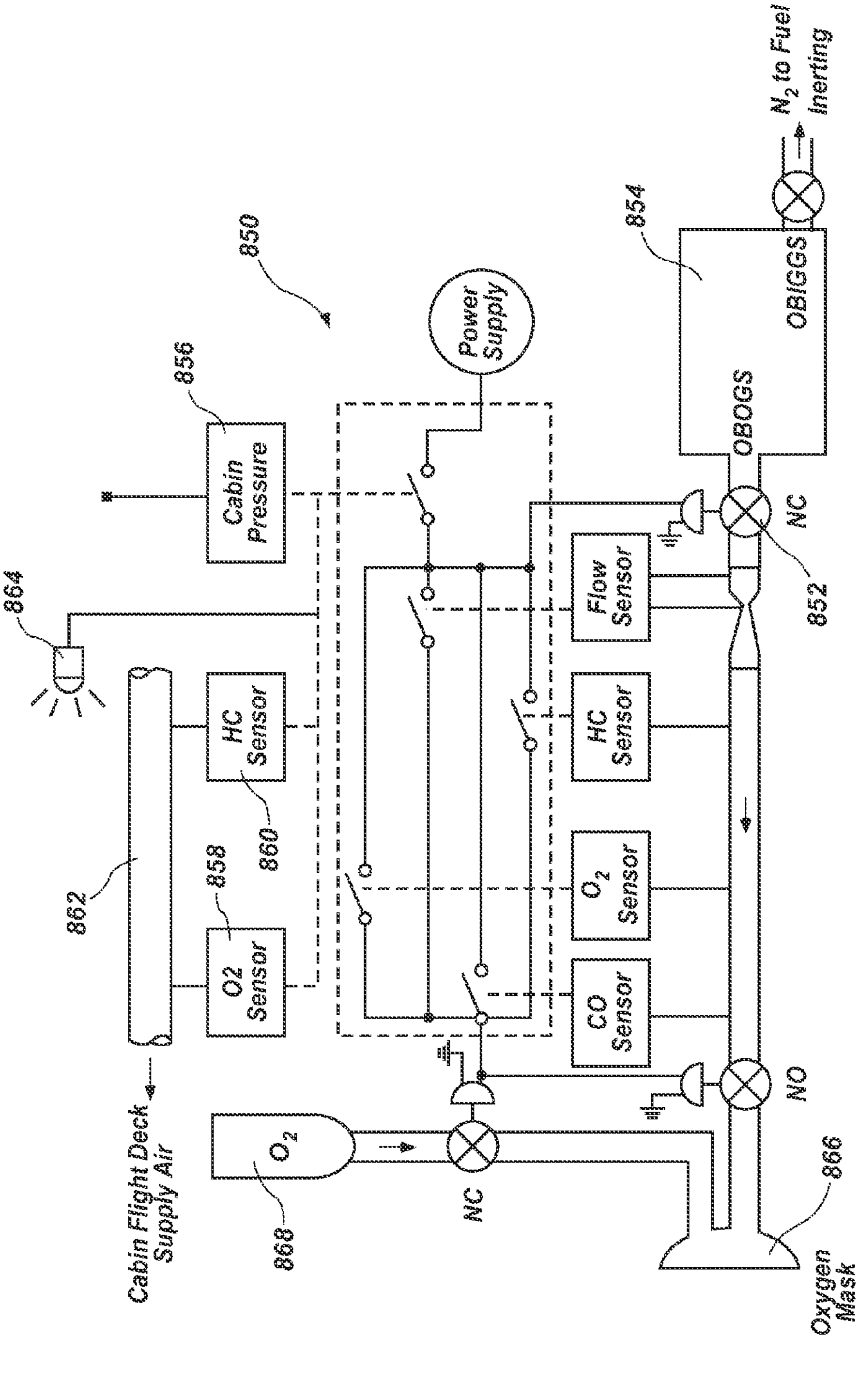
FIG. 8B is a schematic diagram of another embodiment of an automatic on-board oxygen generating system in which the oxygen system can be used for emergency ventilation.

Shown in FIG. 8B is a schematic diagram of another embodiment of an automatic on-board oxygen generating system 850 in which the oxygen system can be used as an emergency ventilation system. Elements in this embodiment that are common with the embodiment of FIG. 8A are not separately labeled in this figure, and are configured to operate as described above. In this configuration an additional power actuated valve 852 is provided at the outlet of the OBOGS device 854. This valve is normally closed ("NC"), and is configured to open whenever the cabin pressure sensor 856 detects a triggering pressure drop, regardless of any triggering of other sensors in the system. In this way, oxygen from the OBOGS can only flow when cabin or cockpit pressure drops below a desired level.

Advantageously, the embodiment of FIG. 8B also allows the oxygen generating system to assist with emergency ventilation. In this embodiment, a CO sensor 858 and hydrocarbon ("HC") sensor 860 are coupled to an air supply line 862 for the cabin or flight deck supply air. If either of these sensors detect a triggering condition, indicating that the main cabin air in line 862 is contaminated (e.g., due to engine or APU lubrication system failure), the OBOGS valve 852 will open, allowing oxygen to flow from the OBOGS device 854 to the oxygen mask(s) 866. This can assist with emergency ventilation of the cabin or cockpit. Additionally, the additional components of the system ensure that the OBOGS supply in this configuration is protected with the backup oxygen bottle 868, in the manner discussed above. An indicator or warning light 864 can be interconnected to the CO and HC sensors 858, 860, so as to provide an indication to the flight crew of contamination in the air supply line 862, in the manner discussed above.

Figure 9:
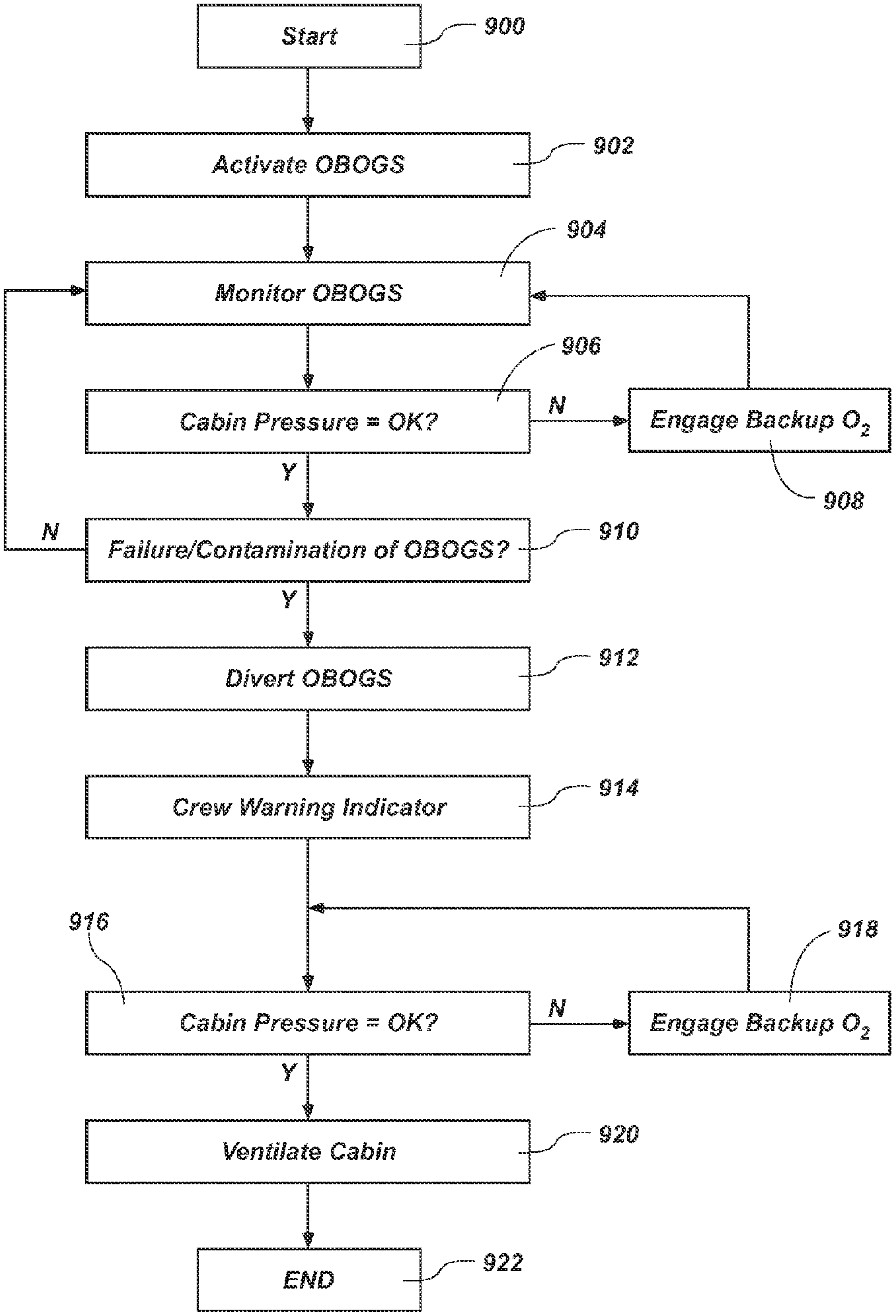
FIG. 9 is a flowchart outlining the steps in one embodiment of a method for providing on-board oxygen generation in an aircraft.

Shown in FIG. 9 is a flowchart outlining the steps in one embodiment of a method for providing on-board oxygen generation in an aircraft. This flowchart diagrams one embodiment of the control logic employed by the monitor (422 in FIG. 4) that controls the system. Following start-up of the system (block 900), the first step is to activate the OBOGS (block 902). Typically, an OBOGS will be running whenever the aircraft engines are running. However, when the aircraft is on the ground, any generated oxygen will be diverted (e.g., exhausted to the atmosphere) since it is not needed in the cabin. As soon as the OBOGS begins operating, the system will monitor it (block 904) to detect any problems with the oxygen or its flow, as discussed above.

The next step is to monitor the cabin or cockpit pressure (block 906). So long as cabin pressure is within an acceptable range, there will be no need to engage the OBOGS to direct oxygen into the cabin or cockpit. This will generally be the case when the aircraft is on the ground or at a relatively low altitude (e.g. below about 10,000 ft.). However, if cabin or cockpit pressure drops below an acceptable level (e.g. 10.1 psia, corresponding to 10,000 ft. altitude), the system engages the OBOGS system to produce oxygen (block 908), and continues monitoring the operation of the OBOGS and the oxygen that flows from that system (block 904). It is to be understood that the term "engage" as used in block 908 is intended to mean the opposite of "divert" as used in block 914. Upon activation of the OBOGS system with the aircraft on the ground, the OBOGS will ordinarily not be engaged, but its oxygen output will normally be diverted out of the aircraft, as indicated above.

So long as no failure or contamination of the OBOGS system is detected, as indicated at query block 910, the system continues operating as normal. However, if a failure or contamination of the OBOGS system is detected, as indicated at query block 910, then the output from the OBOGS system can be diverted (block 912), and a warning indicator provided to the aircraft crew (block 914). At the same time, if cabin pressure is below an acceptable level, as indicated at query block 916 (as would be true in case of cabin depressurization, for example), the backup $O_2$ system is engaged (block 918), in the manner discussed above. In block 918, the term "engage" means to activate the backup $O_2$ system or keep it activated if it is already operating. Blocks 916 and 918 are connected in a loop, indicating that from this point, the system continues to use the backup $O_2$ supply (block 918) until cabin pressure returns to an acceptable level (block 916), whereupon the cabin can be ventilated (block 920). Following this sort of event, the process ends (block 922) and the crew can land the aircraft to allow maintenance and repairs on the OBOGS and/or any related systems.

The process outlined in FIG. 9 allows for a variety of contingencies. For example, when the OBOGS is activated (block 902) but the aircraft is not at altitude (per block 906), and oxygen from the OBOGS is thus not directed into the cabin or cockpit (i.e., the OBOGS is not engaged, block 908), the monitoring (block 904) will continue. Consequently, detection of possible failure of the OBOGS is still continuously considered (block 910). Thus, even if the OBOGS is not engaged to provide oxygen to the cabin or cockpit, the backup systems and steps will proceed. In such a case, the OBOGS will already be diverted as suggested by block 912 (since it is not engaged per block 908), but a warning indicator to the crew (block 914) will be useful to indicate a failure of some kind. Likewise, with the aircraft not at high altitude (block 916), activation of the backup $O_2$ supply (block 918) will not be desired, but ventilation of the cabin (block 920) and eventual shutdown (922) can be undertaken, such as for repairs.

The system disclosed herein thus monitors various factors, such as cabin or cockpit pressure, oxygen flow rate from the OBOGS, oxygen concentration in the air supply, carbon monoxide in the air supply, and hydrocarbon levels in the air supply. Other characteristics can also be monitored. If the cockpit pressure is less than a prescribed limit (e.g. 10.1 psia, which corresponds to 10,000 ft. altitude) then the control logic can allow the oxygen and flow sensors to open the backup oxygen in case of an on-board oxygen-generating system failure. If safe hydrocarbon levels or carbon monoxide levels are exceeded, then the on-board oxygen-generating system supply can be shut-off and the backup oxygen begins to flow. The system thus automatically switches away from the on-board oxygen-generating system supply to the backup oxygen supply when contaminant levels are exceeded or when oxygen flow or concentration is too low while the cabin is above a safe altitude, without requiring specific crew action. This gives the crew time to descend to a safe altitude and/or land the airplane. For ground conditions, there is an indication of contamination and degraded air quality, which can provide warning even before take-off. This would allow for trouble-shooting and a purging operation if necessary.

Compared to some other systems, this oxygen generating system can provide aircraft with better life support systems for pilots, especially for the pilots of military aircraft, to mitigate potential life threatening events, such as breathing contaminated air. This helps avoid the loss of costly aircraft and equipment, as well as the loss of human life.

Although the oxygen-generating system disclosed herein has been described in terms of certain specific embodiments, it is to be understood that other embodiments that are apparent to those of ordinary skill in the art, including embodiments that do not provide all of the features set forth herein, are also within the scope of this disclosure. Those skilled in the art will recognize that the teachings contained herein can be practiced with various modifications within the scope of the claims. Accordingly, the scope of the present disclosure is defined only by reference to the appended claims and equivalents thereof.

What is claimed is:

1. A system for providing oxygen, comprising:

an oxygen generating device, configured to provide oxygenated air;

a monitor of a condition of the air provided by the oxygen generating device;

a backup oxygen supply;

an automatic switch, configured to (i) activate the backup oxygen supply and (ii) block air from the oxygen generating device, when the monitor detects a failure of the condition of the air provided by the oxygen generating device;

a ram inlet;

a monitor of ram pressure; and a ventilation system controller;

wherein said ventilation system controller opens the ram inlet to purge contaminated air inside an aircraft.

2. A system in accordance with claim 1, further comprising a bad air supply warning, cognizable by a user of the system.

3. A system in accordance with claim 1, further comprising an oxygen mask for delivering air from the oxygen generating device or the backup oxygen supply, to a user.

4. A system in accordance with claim 1, wherein the oxygen generating device comprises a zeolite-type oxygen generating device.

5. A system in accordance with claim 1, wherein the monitor is configured to detect at least one of a carbon monoxide (CO) level, an oxygen ($O_2$) level, hydrocarbons, and a flow rate in an outlet of the oxygen generating device.

6. A system for providing oxygen, associated with an aircraft having an interior cabin, comprising:

an oxygen generating device, configured to provide oxygenated air;

a monitor of a condition of the air provided by the oxygen generating device;

a backup oxygen supply;

an automatic switch, configured to (i) activate the backup oxygen supply and (ii) block air from the oxygen generating device, when the monitor detects a failure of the condition of the air provided by the oxygen generating device;

a pressure sensor, configured to detect air pressure within the cabin, the automatic switch being configured to activate the backup oxygen supply when the monitor detects both a failure of the condition of the air provided by the oxygen generating device and the air pressure within the cabin is below a threshold;

a ventilation system; and a ventilation system controller, configured to purge contaminated air from the cabin when the air pressure within the cabin is above the threshold.

7. A system in accordance with claim 1, further comprising a pressurized air source, configured to provide pressurized air to the oxygen generating device.

8. A system in accordance with claim 7, wherein the system for providing oxygen is associated with an aircraft, and the pressurized air source is an engine or auxiliary power unit (APU) of the aircraft.

9. An aircraft, comprising:

an airframe, including a fuselage having an interior, configured to accommodate at least one occupant;

an air supply system, configured to direct oxygenated air to the at least one occupant;

a monitor of condition of air in the air supply system;

a backup oxygen supply;

a controller, configured to (i) activate the backup oxygen supply and (ii) block air from the air supply system, when the monitor detects a failure of the air supply system;

a ventilation system; and a ventilation system controller, configured to purge contaminated air from the interior when the air pressure therein is above a threshold.

10. An aircraft in accordance with claim 9, wherein interior is a cockpit, and further comprising an oxygen mask for the at least one occupant.

11. An aircraft in accordance with claim 9, wherein the interior is a cabin of a passenger aircraft, and further comprising a plurality of oxygen masks for the at least one occupant.

12. An aircraft in accordance with claim 9, wherein the monitor is configured to detect at least one of a carbon monoxide (CO) level, an oxygen ($O_2$) level, hydrocarbons, and a flow rate in an outlet of the air supply system.

13. An aircraft in accordance with claim 9, wherein the air supply system comprises a zeolite-type oxygen generator.

14. A method for providing breathable air to an occupant of an aircraft, comprising:

providing air to the at least one occupant from an air supply;

monitoring a condition of the air;

automatically activating a backup oxygen supply and blocking air from the air supply, upon detection of a failure of the air supply;

drawing air into the aircraft via a ram inlet of a ventilation system; and purging contaminated air from an interior of the aircraft when the air pressure therein is above a threshold.

15. A method in accordance with claim 14, wherein the step of monitoring the condition of the air comprises detecting at least one of a carbon monoxide (CO) level, an oxygen ($O_2$) level, hydrocarbons, and a flow rate in the air supply.

16. A method in accordance with claim 14, wherein air is provided to the at least one occupant via an oxygen mask.

* * * * *